United States Patent [19]
Schultz et al.

[11] Patent Number: 5,340,367
[45] Date of Patent: Aug. 23, 1994

[54] PERMANENT WAVING AND COLOR ENHANCING COMPOSITION AND METHOD

[75] Inventors: Thomas M. Schultz, Ridgefield; Lana Hochman, Sandy Hook, both of Conn.

[73] Assignee: Shiseido Co. Ltd., Tokyo, Japan

[21] Appl. No.: 16,568

[22] Filed: Feb. 11, 1993

[51] Int. Cl.$^5$ ............................................. A61K 7/13
[52] U.S. Cl. ................................................ 8/432; 8/405; 424/72; 132/204; 132/206; 132/208; 132/211
[58] Field of Search ........................... 8/431, 432, 405; 424/72; 132/204, 205, 206, 208, 210, 211

[56] References Cited

U.S. PATENT DOCUMENTS

| | | | |
|---|---|---|---|
| 3,810,478 | 5/1974 | Olson et al. | 424/70 |
| 4,630,621 | 12/1986 | Pontani et al. | 424/70 |
| 4,673,568 | 6/1987 | Grollier et al. | 424/72 |
| 4,798,722 | 1/1989 | Edman et al. | 424/72 |
| 4,906,460 | 3/1990 | Kim et al. | 424/70 |
| 4,970,067 | 11/1990 | Panandiker et al. | 424/70 |
| 5,059,414 | 10/1991 | Dallal et al. | 424/70 |
| 5,161,553 | 11/1992 | Cohen et al. | 132/205 |

FOREIGN PATENT DOCUMENTS

| | | |
|---|---|---|
| 0083095 | 7/1983 | European Pat. Off. |
| 46-38799 | 11/1971 | Japan . |
| 0243011 | 12/1985 | Japan . |

*Primary Examiner*—Paul Lieberman
*Assistant Examiner*—Caroline L. Dusheck
*Attorney, Agent, or Firm*—Melvin I. Stoltz

[57] ABSTRACT

Simultaneous permanent waving and dyeing of hair fibers is attained by incorporating a silk amino acid and a water soluble or emulsifiable silicone based compound in the permanent waving lotion and intermixing the dyestuff with the oxidizing or neutralizing composition. Preferably, the combined dyeing and neutralizing composition is adjusted to have a pH ranging between about 7 and 9. In this preferred embodiment, the hair is warmed after receiving the combined dyeing and neutralizing composition with said composition preferably being processed on the hair at a temperature ranging between 40° C. and 65° C. In addition, further enhanced coloring and permanent waving is attained by incorporating a lipotropic material into the dye additive composition.

22 Claims, No Drawings

PERMANENT WAVING AND COLOR ENHANCING COMPOSITION AND METHOD

TECHNICAL FIELD This invention relates to products for permanently waving hair and, more particularly, to products for permanently waving and concurrently coloring or dyeing the hair.

BACKGROUND ART

In view of the unique composition of hair fibers and the numerous changes that occur in styles and fashion, both the waving of hair and the dyeing of hair have long been of particular interest. In particular, hair color alteration by dyeing while permanent waving hair for long-lasting style retention have long been sought by many individuals. However, due to the composition of hair fiber, either the color or curls are not retained as long as desired and the simultaneous permanent waving and dyeing of hair fibers has not been realized in a broadly useable product.

In order to best understand the reasons for the inability of the hair fiber to retain curls for substantially long time periods or to be simultaneously permanently waved and colored, it is important to understand that hair is composed of a unique protein material called "keratin" and which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S—S) to give keratin protein (K—S—S—K). Only by chemical action can this covalent linkage be broken.

In this regard, many prior art compositions have been developed for the "cold permanent waving" of hair. Typically, these prior art systems treat the hair with a reducing agent which breaks the disulfide (cystine) linkage in the hair. This chemical process typically follows after the hair is wound around a curling rod.

In general, permanent hair waving is usually carried out by subjecting the hair to reagents containing a free—thiol group e.g.,—SH. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations:

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction products formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, typically hydrogen peroxide, and can be illustrated by the following chemical reaction:

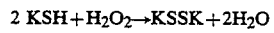

One problem typically found in the prior art occurs when an individual wishes to dye hair which had been permanently waved. In these circumstances, the dye uptake will usually be uneven from the root to the tip of the hair fibers due to the structural alteration caused to the hair fiber by the permanent wave process. In practice, this problem is often circumvented by waiting for the hair to "heal", by allowing for a substantial time interval in which aerial oxidation reseals the excessively damaged areas, thereby providing hair fibers which are more amenable to dye uptake in a level manner.

Consumers have long sought to have a composition and process which would enable both color and permanent waving to be achieved simultaneously. However, no prior art system has been able to provide an effective or reliable composition which would enable simultaneous coloring and permanent waving of hair fibers. In fact, even though this need has existed in the art for decades, no successful commercial product has been attained which satisfies the consumer's need.

Prior to the advance detailed in U.S. Pat. No. 5,094,662, no prior art system existed for effectively permanently waving and permanently dyeing hair simultaneously. In the procedure detailed in this prior art patent, the dye must be incorporated in the permanent waving lotion to provide the permanent dyeing of the hair.

Although the teaching of U.S. Pat. No. 5,094,662 is highly effective in producing results previously unattainable, there is no teaching or suggestion in U.S. Pat. No. 5,094,662 which achieves a long lasting, durable semi-permanent dyeing or coloring for hair wherein the dye is mixed with the neutralizer. It is this area which the present invention has overcome.

The principal concern that has existed in the prior art is that the typical processes used to color hair involve contacting the hair with a mixture of dyes and ammonia and hydrogen peroxide. This combination can cause irreversible damage to the keratin matrix of the hair fiber. Furthermore, in order to be effective, the process requires some mode of swelling of the hair to allow for the penetration of the dye. In the case of tint impartation, whereby the deposited color is a shade or tone lighter than the naturally underlying color, a bleaching of the natural color is required.

Due to the attention that has been given to hair dyeing, the mechanisms involved in the action of dye formation are well understood. In addition, the damage done to the hair fibers is also well-known. In particular, some characteristics of this damage are the dimmunization of the structural integrity of the hair fibers, as evidenced by the loss of resiliency and increased porosity or capability to uptake water.

One principal factor which has led prior art investigators to seek achieving adequate hair dyeing and permanent waving concurrently is the belief that one can capitalize on the increased swelling of the hair which occurs during the reduction step of the permanent wave process. By contacting the hair with a dyestuff composition at this time, greater dye penetration is achieved, as compared to the dye uptake during the typical process of applying hair dyes in a separate process. In addition, by adding the dyestuff to the neutralizing mixture, it is believed that the dyes enter the hair more freely while the hair fibers are in the reduced state.

In spite of the possibility of increased damage to the hair fibers due to the combination of a perming lotion with an oxidative dyestuff composition, the expected longevity of the dyes in hair and the retention of the imparted color were important factors in pursuing this method. The following patents are representative of the prior art technology that has been developed.

In European Patent Application 0260,716A and U.S. Pat. No. 5,161,553, the use of oxidative dyestuffs is disclosed for being applied to hair in the mixture of a neutralizing composition following a permanent wave process. In this teaching, the hair is contacted with a permanent wave lotion while wrapped about a molding rod, rinsed thoroughly and then saturated with a neutralizing composition, typically between 2.2% and 3% hydrogen peroxide. After approximately one-half the time required for neutralizing, the hair is again contacted with the neutralizing composition, but this time a suitable amount of dyestuffs has been added to the composition so as to impart color during the final phase of the process.

Another prior art teaching of using permanent dyestuffs during the neutralizing step is found in U.S. Pat. No. 4,630,621. In this patent, a broad teaching of dyestuffs is claimed to be useful. However, the examples found in the patent focus principally on the use of oxidation dyes. The sole illustration of a direct dye merely employs a derivative of an anthraquinone, which is typically included in permanent hair dyeing compositions only to achieve the blue tones.

Although this patent suggests that the addition of the dyestuffs to the neutralizer attains both an acceptable curl and dye uptake by the hair fibers in a uniform manner, we have found the actual results achieved by employing the processes of the patent are unacceptable. In our experiments, all of which are detailed below, each of the processes defined in the examples of U.S. Pat. No. 4,630,621 were repeated. In each instance, the resulting dyeing and permanent wave characteristics of the hair fibers were significantly weaker than the results attained when the dyestuffs are used without the permanent waving solution.

It is not clear why the process taught in U.S. Pat. No. 4,630,621 results in a minimal dye uptake. However, we believe that there are several explanations as to why the methods taught in this prior art reference fail to deliver acceptable results.

One underlying reason for the failure to obtain intensive coloring may be a result of the attempt to impart dyestuffs into the hair fiber in an acidic medium. The acid pH of the neutralizer composition causes a rapid decrease in hair swelling that could inhibit dye penetration. Consequently, the dyestuffs fail to enter the hair fibers and are removed during the final rinsing.

Another reason is that during permanent waving, the hair is wrapped about a forming rod under tension. The hair is then secured about this rod with an elastic band stretched across the hair bundle, which creates a pressure line where the band is contacting the hair.

Another problem in the prior art is that permanent wave compositions typically contain materials which effectively assist the permanent waving lotion in wetting the hair. For example, proteinaceous quaternary materials, such as are available commercially in the form of Finquat, manufactured by Stepan Chemical Co. of Northfield, Ill. and Maypon, manufactured by Finetex of Elmwood Park, N.J., give the benefit of a conditioned feel to the hair by coating the hair's surface.

Unfortunately, in the presence of such conditioning and wetting agents, the waving lotion inhibits the penetration of such lipophilic materials as coal tar derived dyes while in an aqueous medium, such as the peroxide derived neutralizing compositions commonly employed. The result is an area across at least one section of the hair which does not have an adequate amount of dye uptake. This causes a "banding" effect on the hair fibers, which is clearly undesirable, as it gives poor color results.

This "banding" phenomenon may have been anticipated in U.S. Pat. No. 4,630,621, since the preferred method suggests applying the dye containing solution after the waving lotion has been removed. By employing the suggested method, the majority of the wetting agents are rinsed off, prior to being able to impede the penetration of the dyestuff into the hair.

It is also apparent that other practitioners in this art discovered the phenomenon that conditioning agents affect the dyeing capability when performed concurrently with permanent waving. This realization is evident from the teaching in U.S. Pat. No. 3,368,941 and 3,399,682, wherein hair conditioning materials of the classification of a quaternary amine are shown to be useable with specific dyestuffs of certain classes. In U.S. Pat. No. 3,368,941, acid and metalized dyestuffs are used as pre-existing colored materials. These dyes are attracted to cationic chemicals such as those found in quaternary amine conditioners. While not specifically taught in this patent, hair dyed with this system has limited durability beyond several shampooings. In U.S. Pat. No. 3,399,682, the use of azo dyes is shown to deliver results similar to that of the preceding patent.

Therefore, it is a principal object of the present invention to provide a permanent waving composition and method of application which is capable of providing permanent waving and hair dyeing concurrently.

Another object of the present invention is to provide a permanent waving and hair dyeing composition and method of application having the characteristic features described above which is also capable of providing a long lasting durable semi-permanent coloring to the hair.

Another object of the present invention is to provide a permanent waving composition and process for application thereof having the characteristic features described above which is easy to employ and is capable of providing intense color uptake uniformly distributed along the entire length of the hair fiber.

Other and more specific objects will in part be obvious and will in part appear hereinafter.

DISCLOSURE OF THE INVENTION

By employing the present invention, the prior art difficulties and drawbacks have been eliminated and a composition for simultaneously permanently waving and dyeing hair is achieved. Although the mechanism by which the present invention operates is not fully understood, the compositions and processes detailed herein provide both a remarkable curl and uniform, intense color uptake with a durability associated with long wearing semi-permanent dyes.

Although some prior art teachings have asserted the attainment of this achievement, it has been found that these prior art methods are incapable of providing a uniform, semi-permanent hair dyeing result. However, the present invention is capable of eliminating the adverse effects found in prior art systems and attains a uniform, long-lasting dyed hair fiber, while enabling the hair fibers to be concurrently permanently waved.

In carrying out the present invention, a permanent waving lotion is first applied to the hair in a generally conventional manner. After its application and removal, a neutralizing composition is employed, within which the desired dye composition is intermixed. In order to attain the desired uniform dyeing of the head of hair, while simultaneously permanently waving the head of hair, the permanent wave lotion preferably comprises one selected from the group consisting of thioglycolate salts and esters of thioglycolate salts.

In addition, it has been found that in order to enable the permanent wave lotion to establish hair fibers which are ready for accepting the direct application of the desired dyestuffs, the permanent wave lotion also preferably incorporates silk amino acids and a water soluble or emulsifiable silicone-based compound. By incorporating these two hair enhancing additives into the permanent wave lotion, it has been found that the permanent wave lotion acts upon the hair fibers, in a manner which is not fully understood, but enables the hair fibers to accept the application of the dyestuffs with the neutralizing composition. Throughout this specification, chemical compositions are defined by employing, wherever possible, the accepted designation as is found in the CTFA International Cosmetic Ingredient Dictionary, Fourth Edition, published by the Cosmetic, Toiletry, and Fragrance Association, Washington, D.C. By employing these universally accepted designations throughout the specification, one of ordinary skill in the art will fully understand the chemicals stated herein as well as their formulations as provided in the CTFA International Cosmetic Ingredient Dictionary.

In accordance with the present invention, the permanent wave lotion incorporates silk amino acids and one or more water soluble or emulsifiable silicone based compounds. In the preferred embodiment, the water soluble or emulsifiable silicone based compound comprises one or more selected from the group consisting of dimethicones and amodimethicones. Preferably the silk amino acids employed in the permanent wave lotion comprises between about 0.001% and 2.0% by weight of the total composition, while the silicone-based compound comprises between about 0.001% and 5.0% by weight of the final composition.

Dimethicone is a mixture of fully methylated linear siloxane polymers end blocked with trimethylsiloxy units. Empirically, the formula for dimethicone is $(C_2H_6OSi)_xC_4H_{12}Si$, with the following being representative of its general formula:

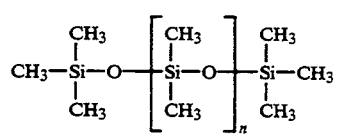

Amodimethicone is a silicone polymer end blocked with amino functional groups. Its formula is represented as follows:

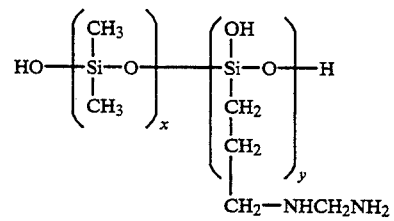

where x has a value of 4 or more.

Although one or a combination of these two water soluble or emulsifiable silicone based compounds are preferred, other substantially equivalent water soluble or emulsifiable silicone based compounds may be employed, without departing from the scope of this invention. One such water soluble or emulsifiable silicone-based compound comprises dimethicone copolyol, which is non-ionic and water soluble, and comprises a polymer of dimethylsiloxane with polyoxyethylene and/or polyoxypropylene side chains.

Another substantially equivalent silicone compound is stearoxytrimethylsilane which is an organo-silicone compound having the empirical formula of $C_{21}H_{46}OSI$. In addition, stearoxy dimethicone may be employed, which is a polymer of dimethylpolysiloxane end blocked with stearoxy groups.

Furthermore, the silicone compound employed in the permanent wave lotion can be a quaternized silicone compound or a betaine silicone compound. A typical quaternized silicone compound is polysiloxane polydimethyl dialkylammonium acetate copolymer. The betaine silicone compound is typified by polysiloxane polyalkyl betaine copolymer.

In Table I, the overall formulation is provided for the preferred permanent waving lotion of the present invention. As stated therein, up to about 20% by weight of the final composition may comprise additives selected to provide enhancements to the final composition. Typically, such additives comprise one or more selected from the group consisting of alkaline agents, penetrating agents, chelating agents, wetting agents, conditioning agents and fragrances. In Table II, detailed formulations are provided for two alternate permanent waving lotions which employ the teaching of this invention.

TABLE I

| Permanent Waving Lotion Composition | |
|---|---|
| Ingredient | Range % by Weight |
| Reducing Agent | 6.0–25.0 |
| Silk Amino Acids | 0.001–2.0 |
| Water Soluble or Emulsifiable Silicone Based Compound | 0.001–5.0 |
| Additives | 0–20 |
| Deionized Water | q.s. to 100% |

TABLE II

| Preferred Permanent Wave Lotion Formulations | | |
|---|---|---|
| Ingredients | Formula A % by Weight | Formula B % by Weight |
| Glyceryl Monothioglycolate | 6–25% | — |
| Glycerin | 2–5% | — |
| Ammonium Thioglycolate (as T-Acid) | — | 6–12% |

TABLE II-continued

| Preferred Permanent Wave Lotion Formulations | | |
|---|---|---|
| Ingredients | Formula A % by Weight | Formula B % by Weight |
| Diammonium Dithiodiglycolate (as DTDG Acid) | — | 2–6% |
| Ammonium Chloride | 1–2% | — |
| Ammonia | 1–5% | 2–5% |
| Styrene/Acrylate Copolymer | — | 0.001–3% |
| Laureth-23 | 1–4% | 1–4% |
| Propylene Glycol | 0.001–5% | — |
| Silk Amino Acids | 0.001–2% | 0.001–2% |
| Trimethylsilylamodimethicone | 0.001–5% | 0.001–5% |
| Octoxynol-40 | 0.001–1% | 0.001–1% |
| Isolaureth-6 | 0.001–1% | 0.001–1% |
| Fragrance | 0.5–2% | 0.5–2% |
| Deionized Water | 60–89% | 70–89% |

Laureth-23 is the polyethylene glycol ether of Lauryl Alcohol (q.v.) that conforms to the formula:

$$CH_3(CH_2)_{10}CH_2(OCH_2CH_2)_nOH$$

where n has an average value of 23.

The permanent wave lotion of this invention is applied to the hair using generally conventional procedures. In this regard, the hair is first wound on rods or rollers, followed by the application of the permanent waving lotion to the hair on the rods. The lotion is then allowed to remain on the hair for between about 5 and 30 minutes. Once the desired processing time has been reached, the lotion is removed by rinsing and towel blotting.

In addition to employing the wave lotion composition detailed above, the preferred embodiment of the present invention has overcome the prior art difficulties by combining the dyestuffs with the neutralization composition, while maintaining the composition at an alkaline pH. Although any alkaline pH level is effective, the preferred pH of the dye/neutralizer composition ranges between 7 and 9. By referring to Table III, the overall formulation for the preferred dye/neutralizer composition is provided.

TABLE III

| Dye/Neutralizer Formulation | |
|---|---|
| Ingredient | Range (% by Weight) |
| Dyestuff | 0.01–5 |
| Hydrogen Peroxide | 1.0–3.0 |
| Alkali to Adjust pH to Range Between 7.0 and 9.0 | |
| Additives | 0–20 |
| Deionized Water | q.s. to 100% |

A further unique aspect of the present invention is the additional discovery that the application of heat to the hair during the neutralizing process provides substantially enhanced, beneficial results. This discovery is believed to be particularly unique, since no prior art references teaches or suggests the application of heat to the hair during these procedures.

In the present invention, it has been found that the hair should be warmed while the dye/neutralizer composition is saturated on the hair. In addition, it has been found that the optimum benefit is realized when the hair is warmed to between about 40° C. and 65° C. By employing this warming process, both the penetration and levelness of the dyes about the hair fibers are maximized.

In the preferred embodiment, a dye additive composition is prepared and intermixed with the neutralizing composition prior to use. The principal ingredient in this composition is the particular dye or combination of dyes selected to attain the desired coloring. Although not intended as an exhaustive testing of all of the dyes employable in this invention, Table IV identifies the principal dyestuffs which have been found to be effectively employable using the teaching of the present invention.

TABLE IV

| Dyestuffs | | |
|---|---|---|
| HC Blue No. 2 | HC Red No. 3 | Disperse Black 9 |
| HC Blue No. 4 | HC Yellow No. 2 | Disperse Blue 1 |
| HC Blue No. 5 | HC Yellow No. 3 | Disperse Blue 3 |
| HC Orange No. 1 | HC Yellow No. 4 | Disperse Violet 1 |
| HC Red No. 1 | HC Yellow No. 5 | Disperse Violet 4 |
| | | Acid Orange No. 3 |

It has also been discovered that the present invention is able to achieve further efficacious results by incorporating a lipotropic material into the dye additive composition. Due to its cationic nature, the lipotropic material is extremely substantive to hair. It possesses excellent spreading properties on hair to help improve color evenness, in addition to imparting lustre and improving manageability. Preferably, the lipotropic material employed in the composition comprises a chemical structure capable of delivering a lipophilic material in an aqueous medium to a lipid environment, such as the direct dyes used in the application of the neutralizing composition to hair fibers.

In the preferred embodiment of the present invention, the lipotropic materials comprise the derivatives of vegetable derived amino acids substituted with one or more moieties selected from the group consisting of lauryl-, stearoyl-, and cocoyl-methylamine. In addition, it has been found that the lipotropic materials perform most efficaciously when incorporated into the dye additive composition at a concentration ranging between about 0.001% and 2.5% by weight.

By referring to Table V, the preferred formulation for the dye additive is provided. In addition, in Table VI, formulations for two alternate preferred neutralizer compositions are detailed. As shown in Table VI, the preferred neutralizer composition incorporates a silk amino acid and a water soluble or emulsifiable silicone based compound in addition to a generally conventional neutralizer formulation. Although not mandatory, the incorporation of a silk amino acid and a water soluble or emulsifiable silicone compound into the neutralizer has been found to provide a further enhanced beneficial result to the simultaneous permanent waving and coloring of the hair in accordance with this invention.

TABLE V

| Preferred Dye Additive Formulation | |
|---|---|
| Material | WT. % |
| Dyes (selected from Table IV) | 0.01–5 |
| Ethanolamine | 0–1 |
| Ethoxydiglycol | 0–2 |
| Glycoproteins | 0–2 |
| Hydroxyethylcellulose | 0–2 |
| Lauryloleylmethylamine | 0.001–2.5 |
| Soy Amino Acids (Lipotrope) | |
| PEG-8 Hydrogenated Tallow Amine | 0–5 |
| Tetrasodium EDTA | 0–1 |
| Fragrance | 0–2 |
| Deionized Water | 78–99 |

TABLE VI

Preferred Neutralizer Formulations

| Material | Formula A % by Weight | Formula B % by Weight |
|---|---|---|
| Sodium Lauryl Sulfate | 0–2 | 0–2 |
| Cetearyl Alcohol | 0–2 | 0–2 |
| Ceteth-20 | 0–2 | 0–2 |
| Mineral Oil | 0–2 | |
| Hydrogen Peroxide | 1–3 | 1–3 |
| Disodium Phosphate | 0–2 | 0–2 |
| Phosporic Acid | 0–2 | 0–2 |
| Olealkonium Chloride | 0–2 | 0–2 |
| Silk Amino Acids | 0.001–2 | |
| Trimethylsilylamodiumethicone | 0.001–5 | |
| Octoxynol-40 | 0–1 | |
| Isolaureth-6 | 0–1 | |
| Dimethicone | | 0.001–3 |
| Cyclomethicone | | 0.001–3 |
| Propylene | 0–5 | 0–5 |
| Methyl Paraben | 0–2 | 0–2 |
| Fragrance | 0–2 | 0–2 |
| Deionized Water | 65–98 | 68–98 |

Ceteth-20 is the polyethylene glycol ether of Cetyl Alcohol (q.v.) that conforms to the formula:

$$CH_3(CH_2)_{14}CH_2(OCH_2CH_2)_nOH$$

where n has an average value of 20.

Octoxynol-40 is the ethoxylated alkyl phenol that conforms generally to the formula:

$$C_8H_{17}C_6H_1(OCH_2CH_2)_nOH$$

where n has an average value of 40.

Isolaureth-6 is the polyethylene glycol other of branched chain aliphatic 12 carbon alcohols. It conforms generally to the formula:

$$C_{12}H_{25}(OCH_2CH_2)_nOH$$

where n has an average value of 6.

Any of the silicone compounds detailed above may be employed in the neutralizer. Similarly, as detailed above, one or more selected from the group consisting of dimethicones and amodimethicones is preferred.

Using the formulation detailed above, the dye additive mixture and the neutralizer mixture are combined to form a dye and neutralizing composition for application to the hair. In accordance with the preferred process of the present invention, once the permanent wave lotion has been removed from the hair fibers, a portion of the dyeing and neutralizing composition is applied to the hair wound on the rods. After allowing a processing time of between about 3 minutes and 5 minutes, the rods are removed from the hair fibers. Then, the remaining dyeing and neutralizing composition is applied to the hair fibers, and allowed to remain on the hair for between about 5 minutes and 15 minutes.

As detailed above, in the preferred application process, heat is applied to the hair after the application of the dyeing and neutralizing mixture to the rod-free hair. Although the hair can be heated for between about 2 minutes and 15 minutes, it has been found that the hair should be heated for substantially the entire processing time of the dyeing and neutralizing mixture on the rod-free hair. Once this processing time has been completed, the hair is allowed to cool for between 1 and 2 minutes. Then, the dyeing and neutralizing mixture is rinsed from the hair.

By employing the permanent wave lotion and dyeing and neutralizing composition of this invention, the prior art difficulties are virtually eliminated and resilient, permanently waved hair fibers are produced along with uniform, intense, durable simultaneously coloring being imparted thereto.

The invention accordingly comprises a composition possessing the features, proportions and the relation of constituents, as well as the several steps and the relation of one or more such steps with respect to each of the other, all as fully detailed herein, with the scope of the invention being indicated in the claims.

BEST MODE FOR CARRYING OUT THE INVENTION

In order to demonstrate the unique capabilities of the present invention and prove the efficacy of the formulations and processes detailed herein, the following examples are provided. Although these examples are intended as a teaching of the best mode for carrying out the present invention, the examples are not intended to limit, in any manner, the breadth of this discovery.

By employing the permanent waving and hair dyeing compositions of this invention, as well as the application methods detailed herein, hair fibers are simultaneously permanently waved and dyed in a manner which attains both long lasting curl retention and improved dye retention. Unless otherwise stated, the methods defined above were employed in conducting the following tests. Furthermore, in order to provide repeatable, objective, quantitative measurements of the hair coloring and durability achieved by the present invention, a colorimeter was employed, with the dyed hair samples being tested for color permanency, durability and washability.

A colorimeter measures the intensity of lightness, hues and tones of the hair, as delineated in the C.I.E. Scale for color measurements. In these measurements, the chromaticity values of "L", "a", and "b", are employed, wherein "L" equals the total reflectance of the hair fiber, with black equal to a value of zero and white equal to a value of one hundred. In addition, "a" equals a positive value for red and a negative value for green while "b" equals a positive value for yellow and a negative value for blue. For consistency, all measurements were taken employing a Spectroguard II system from Pacific Scientific Instruments, or a Chromameter CR-300 from Minolta.

In order to further quantify the measurements taken and compare the results achieved in the present invention with the results achieved in the prior art, the following equation was employed. In this equation ΔE is employed to quantitatively represent the overall color change or resulting color effect.

$$\Delta E = \sqrt{(L_t - L_c)^2 + (a_t - a_c)^2 + (b_t - b_c)^2}$$

where
c = value of control, and
t = measurement of test samples using the present invention.

Example 1

The tests performed in this example were designed to show the benefit attained by incorporating silk amino acids and a water soluble or emulsifiable silicone compounds in the permanent wave lotion prior to the application of the dye and by heating the hair during the dye application step. In these tests, tresses of hair were processed using an acid permanent waving lotion into which silk amino acids and a silicone blend of dimethicone and amodimethicone were added, as detailed above. As a control or baseline comparison, an acid permanent waving lotion without the silk amino acid and the blend of dimethicone and amodimethicone was applied to separate tresses of hair.

In these tests, the acid permanent waving lotion employed as the control was the "Quantum" permanent wave lotion which is manufactured by Helené Curtis Corporation of Chicago, Ill.

The permanent wave lotions were applied and removed following identical conventional procedures. Then, a dye/neutralizing composition was prepared and applied to the tresses of hair. In each instance, a composition consisting of a blend of direct dyes, totaling between about 0.5% and 15% by weight and selected from Table IV to give the desired natural brown shade, was added to the conventional neutralizer at a ratio of one part color composition to four parts neutralizer. This resulted in a total dye concentration of between about 0.1% to 3% by weight.

Once prepared, a portion of the color/neutralizer mixture was applied to the hair tresses wound on the rods. After five minutes of exposure, the rods were removed and the remaining color/neutralizer mixture was applied to the shaft and ends of the hair fibers. Once the application of the mixture was completed, the tresses of hair were processed with heat at about 45° C. for ten minutes, while the color/neutralizer mixture remained on the hair. Thereafter, the tresses of hair were allowed to cool for one minute and then rinsed.

Observations of the permanently waved and dyed hair tresses showed that the hair tresses which were heated and treated with the permanent wave composition incorporating the silicone blend and the silk amino acids achieved an increased dye uptake over the hair tresses treated in the identical manner, but without the silk amino acids and the silicone blend.

After the initial observations, the hair tresses were exposed to three separate cycles of shampooing and drying, and then re-evaluated. These observations show that the hair tresses treated with the silicone blend and the silk amino acids attained both improved initial color deposit and color durability over the hair tresses not treated with the additives to the permanent wave lotion. All of the test results obtained from this example are detailed in Table VI.

TABLE VI

| Efficacy of Additives in the Waving Lotion | | | | |
|---|---|---|---|---|
| | Chromaticity Values | | | |
| | L | a | b | ΔE |
| Quantum by Helene Curtis | | | | |
| After Permanent Waving and Dyeing | 31.64 | 4.23 | 15.88 | |
| After Three Shampoo/Drying Cycles | 38.12 | 3.56 | 19.33 | 7.37 |
| Modified Permanent Waving Lotion (Containing Additives) | | | | |
| After Permanent Waving and Dyeing | 30.04 | 6.22 | 15.00 | |
| After Three Shampoo/Drying Cycles | 32.68 | 5.59 | 17.12 | 3.44 |

EXAMPLES 2-3

In order to prove the ability of the present invention to overcome the drawbacks encountered in the prior art, tresses of hair were processed in accordance with the teachings of Examples I and II of U.S. Pat. No. 4,630,621. In conducting these tests, the acid perm employed was ACCLAIM which is manufactured and distributed by Zotos International of Darien, Conn. In addition, the processing time employed for the permanent waving lotion was twenty-five minutes.

The dye employed was Miss Clairol Shade 45 R-Light Auburn, which is manufactured by Clairol of New York, N.Y. Four percent by weight of this dye mixture was added to the neutralizer and the color/neutralizer mixture was applied in the manner detailed in Example I of U.S. Pat. No. 4,630,621. In accordance with that process, the dye/neutralizer mixture was applied to the hair on the rods and allowed to remain for five minutes. The rods were then removed, and the product was worked through the hair and processed for an additional five minutes before rinsing.

After completion of this process, observations showed that very little color was deposited on the hair tresses. In addition, uneven coverage was found from root to end. This poor color performance is evident in Table VII, wherein the overall test results are provided.

TABLE VII

| Dye Uptake Using Prior Art Method | | | |
|---|---|---|---|
| | Chromaticity Values | | |
| | L | a | b |
| White Hair (Standard) | 74.12 | −1.48 | 18.19 |
| Process of Examples I and II of U.S. Pat. No. 4,6320,621 - at hair root | 64.49 | 6.43 | 20.39 |
| Process of Examples I and II of U.S. Pat. No. 4,630,621 - at hair shaft | 66.79 | 4.49 | 18.92 |
| Process of Examples I and II of U.S. Pat. No. 4,630,621 - at hair end | 67.15 | 3.93 | 19.97 |
| Process of Examples I and II of U.S. Pat. No. 4,630,621 - overall average | 66.14 | 4.95 | 19.76 |

A plurality of hair tresses were tested using the process defined in Example III of U.S. Pat. No. 4,630,621. In addition, the same procedure was followed along with certain modifications, detailed herein, in order to compare the results of the present invention with this prior art teaching.

In performing these tests, an auburn semi-permanent color was added to the neutralizer at a ratio of one part color to two parts neutralizer. In accordance with the teaching of Example III of U.S. Pat. No. 4,630,621, the neutralizer, without the color added, was first applied to the hair while wound on rods. Then, the color/neutralizing mixture was applied. After allowing the color/neutralizer mixture to remain on the hair for five minutes, the rods were removed and the product was worked through the hair. After an additional five minutes, the hair was rinsed.

Observations of the hair tresses produced by employing this procedure, without any modification, showed a weak dyeing of the hair with the color being deposited unevenly along the hair fibers. In particular, the ends were lighter than the hair roots and shafts. The chromaticity values obtained are shown in Table VIII.

In order to test the efficacy of the present invention over this prior art teaching, hair samples were dyed using the procedure detailed above, as defined in Example III of U.S. Pat. No. 4,630,621, along with some modifications. In this modified test procedure, the color/neutralizer mixture was applied to the hair while wound on the rods, without a pre-application of the colorless neutralizer. After five minutes, the rods were removed, and the color/neutralizer mixture was worked through the hair. In addition, the hair tresses were processed with heat after the color/neutralizer mixture had been worked through the hair following the removal of the rods. In applying the heat, a plastic bag was placed over the hair and heat was applied for five minutes at a temperature of about 45° C. After this heat application, the hair was allowed to cool to room temperature, for about one minute, and was then rinsed.

Observations of the auburn hair fibers resulting from this modified process showed substantially improved dye uptake, with a more even coloring resulting along the entire length of hair from its root to its end. The chromaticity values obtained using this modified process are shown in Table VIII.

In order to test the durability of the resulting dye on both the prior art process and the modified process, the hair tresses were subjected to two shampoo and drying cycles, directly after the application of the permanent waving lotion and dye/formulation. Observations after the shampoo/drying cycles showed more color was retained in the hair employing the modified process than was retained by the hair fibers processed in accordance with the procedure of Example III of U.S. Pat. No. 4,630,621. The test results from these procedures are detailed in Table VIII.

TABLE VIII

Efficacy of Modified Process and Using Heat

| | Chromaticity Values | | | |
|---|---|---|---|---|
| | L | a | b | ΔE |
| After Permanent Waving and Dyeing | | | | |
| -U.S. Pat. No. 4,630,621 (Example III) | 38.40 | 26.24 | 22.95 | |
| -Modified Process and Heat | 28.18 | 24.65 | 28.33 | 11.37 |
| After Permanent Waving and Dyeing and Two Shampoo/Dry Cycles | | | | |
| -U.S. Pat. No. 4,630,621 (Example III) | 47.62 | 23.22 | 25.61 | |
| -Modified Process and Heat | 36.15 | 23.48 | 22.69 | 11.83 |

As shown by the test results detailed in Table VIII, applying the neutralizer before applying the color/neutralizer mixture, as taught by U.S. Pat. No. 4,630,621, resulted in reduced dye penetration or deposit. However, by employing the modified process of the present invention and heating the hair while the dye remained on the hair fibers, dye uptake was improved as well as wearability and permanency of the color.

EXAMPLE 4

In order to further confirm the efficacy of the present invention and the substantially improved results attained by employing the teaching of this invention, further comparative experiments were conducted. In these tests, tresses of hair were tested following the process detailed in Example III of U.S. Pat. No. 4,630,621 as well as using a modification to that process as taught herein. In all tests, an acid perm and a natural brown dye were used, with the dye being added to the neutralizer in a ratio of 1:4.

The control test samples were permanently waved and dyed using the teaching found in Example III of U.S. Pat. No. 4,630,621. This procedure, with the prior art control samples, is fully detailed above in Example 2. In order to compare the teaching of the present invention with the prior art control samples, the following modifications were made. Firstly, the acid perm was modified by incorporating therein 0.001-2% by weight of silk amino acids and 0.001%-5% by weight of a silicone blend of dimethicones and amodimethicones.

In addition to employing silk amino acids and the silicone blend in the permanent wave lotion, the experimental hair tresses were neutralized using the modified process in accordance with this invention. In this modified process, no pre-application of the neutralizer was made. Instead, the color/neutralizer mixture was applied to natural white hair, purchased from DeMeo Brothers in New York. The hair was wound on the rods and allowed to stand for five minutes. Thereafter, the color/neutralizer mixture was applied to the natural white hair after the rods were removed and allowed to stand for an additional ten minutes. Furthermore, during this ten minutes, heat was applied to the hair at about 45° C.

Once the tresses of hair were permanently waved and dyed, observations of the hair tresses were made. The hair fibers employed in the prior art process exhibited significantly less dye uptake than the hair fibers resulting from the modified procedure and formulations of this invention. The test results attained from these experiments are provided in Table IX. In addition, the test results attained after shampooing and drying the hair tresses three times after perming and drying are also provided in Table IX.

TABLE IX

Efficacy of Present Invention

| | Chromaticity Values | | | |
|---|---|---|---|---|
| | L | a | b | ΔE |
| After Permanent Waving and Dyeing | | | | |
| -U.S. Pat. No. 4,630,621 (Example III) | 46.43 | 5.10 | 17.57 | |
| -Modified Process and Heat | 30.04 | 6.22 | 15.00 | 17.16 |
| After Permanent Waving and Dyeing and Two Shampoo/Dry Cycles | | | | |
| -U.S. Pat. No. 4,630,621 (Example III) | 51.53 | 4.18 | 18.46 | |
| -Modified Process and Heat | 32.68 | 5.59 | 17.12 | 18.95 |

As is evident from these test results, the hair tresses processed with the modified methods and formulations of the present invention resulted in hair fibers exhibiting substantially improved dye uptake. In addition, these hair fibers possessed substantially improved or prolonged color wearability, as is evident from the results exhibited after three separate shampoo and dry cycles.

EXAMPLE 5

In this series of tests, two different hair dye formulations, namely golden brown and auburn, were evaluated, both with and without the application of heat. By employing these tests, the dye uptake achieved by using heat was determined for totally different hair dye formulations. The hair tresses processed with heat were exposed to heating at a temperature ranging between about 40° C. and 50° C. Furthermore, after observation of the results, the hair tresses were exposed to three separate and independent shampoo and drying cycles and then evaluated again to determine the wearability or durability of the color.

In all of these tests, the color was added to the neutralizer in a ratio of 1:4. In addition, all of the tests were conducted using the modified procedure detailed above in Example 4. In this procedure, the color/neutralizing mixture, was applied to the hair fibers when wound on curling rods and allowed to stand for five minutes. Then, the rods were removed and the hair was processed for an additional ten minutes either at room temperature, or with exposure to heat. The test results obtained are detailed below in Table X.

TABLE X

|  | Chromaticity Values | | | |
| --- | --- | --- | --- | --- |
|  | L | a | b | Δ |
| GOLDEN BROWN | | | | |
| After Permanent Waving and Dyeing | | | | |
| -At Room Temperature | 39.25 | 7.59 | 18.01 | |
| -With Heat | 29.48 | 7.51 | 15.54 | 10.07 |
| After Three Shampoo/Drying Cycles | | | | |
| -At Room Temperature | 40.91 | 6.80 | 18.09 | |
| -With Heat | 33.74 | 6.93 | 18.71 | 7.19 |
| AUBURN | | | | |
| After Permanent Waving and Dyeing | | | | |
| -At Room Temperature | 36.09 | 24.69 | 22.50 | |
| -With Heat | 32.08 | 25.11 | 21.45 | 4.16 |
| After Three Shampoo/Drying Cycles | | | | |
| -At Room Temperature | 39.44 | 22.98 | 23.62 | |
| -With Heat | 36.53 | 23.47 | 23.88 | 2.96 |

As is evident from the results detailed in Table X, significantly greater color uptake was obtained on the hair fibers processed with heat, regardless of which shade of dye was employed. In addition, the color durability or retention for the hair fibers processed with heat was substantially greater with both hair dye colors, as compared to the application of the hair dye at room temperature. As is evident from these results, the application of heat during the neutralizing step produces substantially improved results.

As is now evident from a review of all of the foregoing examples, substantially improved concurrent hair dyeing and permanent waving results are obtained by employing the procedures and formulations of this invention, while the prior art difficulties and drawbacks have been substantially eliminated. Furthermore, both improved color uptake and color durability are realized.

Based upon the foregoing teaching, optimum dye uptake and durability are obtained by incorporating silk amino acids and a silicone blend into the permanent wave lotion, while also maintaining the color/neutralizing mixture at an alkaline pH. Furthermore, heat is preferably applied to the hair during the final color/neutralizer application.

A further critically important process step discovered in the present invention, which distinguishes the present invention over prior art teachings, is the application of the color/neutralizer mixture directly to the reduced hair, without first applying the neutralizer without any dye to the hair fibers. As is evident from the test results obtained, the application of the color-free neutralizer prior to the color/neutralizer mixture causes the dye penetration to be inhibited, thereby reducing the dye uptake. However, by applying the color/neutralizer mixture directly to the reduced hair, substantially improved coloring is achieved, as well as substantially improved color durability.

Finally, it has also been found that additional beneficial results are obtained by incorporating a lipotropic material into the dye additive of the dye/neutralizer mixture. In addition, the incorporation of silk amino acids and water soluble or emulsifiable silicones in the neutralizer of the dye/neutralizing mixture provides additional enhancements.

It will thus be seen that the objects set forth above, among those made apparent from the preceding description, are efficiently attained and, since certain changes may be made in the compositions detailed herein, as well as in carrying out the above process, without departing from the scope of the invention, it is intended that all matter contained in the above description shall be interpreted as illustrative and not in a limiting sense.

It is to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients whenever the sense permits.

What is claimed is:

1. A system for simultaneously permanently waving and coloring hair, said system comprising:
   A. a permanent wave lotion for application to the hair for breaking the disulfide linkages in the hair, said lotion comprising
      a. between about 6% and 25% by weight of a reducing agent selected from the group consisting of thioglycolate salts and esters of thioglycolate salts,
      b. between about 0.001% and 2.0% by weight of a silk amino acid,
      c. between about 0.001% and 5.0% by weight of a water soluble or emulsifiable silicone based compound, and
      d. water forming the balance; and
   B. a dyeing and neutralizing composition for application to the hair after the removal of the permanent waving lotion, said dyeing and neutralizing composition being formed by intermixing
      a. a dye additive composition comprising
         1. between about 0.001% and 5% by weight of one or more dyestuffs for providing the desired color to the hair,
         2. between about 0.001% and 2.5% by weight of a lipotropic material comprising vegetable-derived amino acids amidified with and containing one or more moieties selected from the group consisting of cocoylo-methylamine, lauryl, and stearoxyl,
         3. an alkali for maintaining the pH of the dyeing and neutralizing composition to between about 7 and 9, and
         4. water forming the balance; and
      b. a neutralizing composition comprising
         1. between about 1.0% and 3.0% by weight of hydrogen peroxide, and
         2. water forming the balance;
   whereby the serial application of the permanent waving lotion and the dyeing and neutralizing composition provides permanent waving of the hair and simultaneous dyeing thereof with a durable, long-lasting, semi-permanent coloring being imparted thereto.

2. The system defined in claim 1, wherein the dyeing and neutralizing composition is further defined as being processed on the hair with heat.

3. The system defined in claim 2, wherein the neutralizing composition is further defined as being processed on the hair at a temperature ranging between 40° C. and 65° C.

4. The system defined in claim 1, wherein the dyestuff of the dyeing and neutralizing composition is further defined as comprising one or more selected from the group consisting of HC Blue No. 2, HC Blue No. 4, HC Blue No. 5, HC Orange No. 1, HC Red No. 1, HC Red No. 3, HC Yellow No. 2, HC Yellow No. 3, HC Yellow No. 4, HC Yellow No. 5, Disperse Black 9, Disperse Blue 1, Disperse Blue 3, Disperse Violet 1, Disperse Violet 4, and Acid Orange No. 3.

5. The system defined in claim 1, wherein the water soluble or emulsifiable silicone based compounds of the permanent waving lotion is further defined as comprising one or more selected from the group consisting of dimethicones, amodimethicones, dimethicone copolyol, stearoxytrimethylsilane, stearoxydimethicones, quaternized silicone compounds, and betain silicone compounds.

6. The system defined in claim 5, wherein the water soluble or emulsifiable silicone based compound is further defined as comprising one or more selected from the group consisting of dimethicones and amodimethicones.

7. The system defined in claim 5, wherein the permanent waving lotion is further defined as comprising up to 20% by weight of one or more additives selected from the group consisting of alkaline agents, penetrating agents, chelating agents, wetting agents, conditioning agents and fragrances.

8. The system defined in claim 7, wherein the additives of the permanent waving lotion are further defined as comprising:
 e. between about 1% and 2% by weight of ammonium chloride,
 f. between about 1% and 5% by weight of ammonia,
 g. between about 1% and 4% by weight of laureth-23 of the general formula $CH_3(CH_2)_{10}CH_2(OCH_2CH_2)_nOH$, wherein n has an average value of 23,
 h. between about 0.001% and 5% by weight of propylene glycol,
 i. between about 0.001% and 1% by weight of octoxynol-40 of the general formula $C_8H_{17}C_6H_4(OCH_2CH_2)_nOH$, wherein n has an average value of 40,
 j. between about 0.001% and 1% by weight of isolaureth-6 of the general formula $C_{12}H_{25}(OCH_2CH_2)_nOH$, wherein n has an average value of 6, and
 k. between about 0.5% and 2% by weight of a fragrance.

9. The system defined in claim 7, wherein the additives are further defined as comprising
 e. between about 2% and 5% by weight of ammonia,
 f. between about 0.001% and 3% by weight of styrene/acrylate copolymer,
 g. between about 1% and 4% by weight of laureth-23 of the general formula $CH_3(CH_2)_{10}CH_2(OCH_2CH_2)_nOH$, wherein n has an average value of 23,
 h. between about 0.001% and 1% by weight of octoxynol-40 of the general formula $C_8H_{17}C_6H_4(OCH_2CH_2)_nOH$, wherein n has an average value of 40,
 i. between about 0.001% and 1% by weight of isolaureth-6 of the general formula $C_{13}H_{25}(OCH_2CH_2)_nOH$, wherein n has an average value of 6, and
 j. between about 0.5% and 2% by weight of a fragrance.

10. The dye additive composition defined in claim 1, wherein the dye additive composition is further defined as comprising
 5. up to 1% by weight of ethanolamine,
 6. up to 2% by weight of ethoxydiglycol,
 7. up to 2% by weight of glycoproteins,
 8. up to 2% by weight of hydroxyethylcellulose,
 9. up to 5% by weight of PEG-8 hydrogenated tallow amine,
 10. up to 1% by weight of tetrasodium EDTA, and
 11. up to 2% by weight of fragrance.

11. The neutralizer composition defined in claim 1, wherein said neutralizer composition is further defined as comprising
 3. between about 0.001% and 5% by weight of a water soluble or emulsifiable silicone based compound, and
 4. between about 0.001% and 2% by weight of silk amino acid.

12. The neutralizer composition defined in claim 11, wherein the neutralizer composition is further defined as comprising
 5. up to 2% by weight of sodium lauryl sulfate,
 6. up to 2% by weight of cetearyl alcohol,
 7. up to 2% by weight of ceteth-20 of the general formula $CH_3(CH_2)_{14}CH_2(OCH_2CH_2)_nOH$, wherein n has an average value of 20,
 8. up to 2% by weight of mineral oil,
 9. up to 2% by weight of disodium phosphate,
 10. up to 2% by weight of phosphoric acid,
 11. up to 2% by weight of olealkonium chloride,
 12. up to 1% by weight of octoxynol-40 of the general formula $C_8H_{17}C_6H_4(OCH_2CH_2)_nOH$, wherein n has an average value of 40,
 13. up to 1% by weight of isolaureth-6 of the general formula $C_{12}H_{25}(OCH_2CH_2)_nOH$, wherein n has an average value of 6,
 14. up to 5% by weight of propylene glycol,
 15. up to 2% by weight of methyl parabin, and
 16. up to 2% by weight of a fragrance.

13. A process for simultaneously permanently waving and coloring hair comprising the steps of:
 A. preparing a permanent waving lotion for application to the hair comprising
  a. between about 6% and 25% by weight of a reducing agent selected from the group consisting of thioglycolate salts and esters of thioglycolate salts,
  b. between about 0.001% and 2.0% by weight of a silk amino acid,
  c. between about 0.001% and 5.0% by weight of a water soluble or emulsifiable silicone based compound, and
  d. water forming the balance;
 B. applying the permanent waving lotion to the hair and allowing the lotion to remain on the hair for the desired processing time;
 C. removing the permanent waving lotion from the hair;
 D. forming a dyeing and neutralizing composition for application to the hair comprising
  a. between about 0.01% by weight and 5% by weight of one or more dyestuffs selected for imparting the desired coloring to the hair,
  b. between about 1.0% and 3% by weight of hydrogen peroxide, and
  c. water forming the balance;

E. adjusting the pH of the dyeing and neutralizing composition to range between about 7.0 and 9.0;

F. applying the dyeing and neutralizing composition to the hair and allowing the composition to remain on the hair for the desired processing time;

G. warming the hair after the application of the dyeing and neutralizing composition through a portion of the processing time thereof; and H. rinsing the dyeing and neutralizing composition from the hair, thereby obtaining a permanently waved head of hair which also incorporates precisely desired color imparted to the hair fibers in a manner which provides both uniformity and durability.

14. The process defined in claim 13, wherein the dyestuff incorporated into the dyeing and neutralizing composition is further defined as comprising one or more selected from the group consisting of HC Blue No. 2, HC Blue No. 4, HC Blue No. 5, HC Orange No. 1, HC Red No. 1, HC Red No. 3, HC Yellow No. 2, HC Yellow No. 3, HC Yellow No. 4, HC Yellow No. 5, Disperse Black 9, Disperse Blue 1, Disperse Blue 3, Disperse Violet 1, Disperse Violet 4, and Acid Orange No. 3.

15. The process defined in claim 13, wherein the hair is warmed to a temperature ranging between about 40° C. and 65° C.

16. The process defined in claim 15, comprising the additional steps of

I. placing the hair on rods or rollers prior to the application of the permanent waving lotion;

J. applying a portion of the dyeing and neutralizing composition to the hair while on the rollers, after the removal of the permanent waving lotion and allowing the lotion to remain on the hair for between about 3 and 8 minutes;

K. removing the rods or rollers from the hair;

L. applying the remainder of the dyeing and neutralizing composition to the hair fibers and allowing the composition to remain on the hair for between about 5 and 15 minutes;

M. warming the hair after the application of the dyeing and neutralizing composition to the rod-free hair fibers; and N. allowing the hair to cool for between about 1 and 2 minutes prior to rinsing the dyeing and neutralizing composition from the hair.

17. A process for simultaneously waving and coloring hair comprising the steps of:

A. preparing a permanent waving lotion for application to the hair comprising:
  a. between about 6% and 25% by weight of a reducing agent selected from the group consisting of thioglycolate salt and esters of thioglycolate salts,
  b. between about 0.001% and 2.0% of a silk amino acid,
  c. between about 0.001% and 5.0% by weight of a water soluble or emulsifiable silicone based compound,
  d. up to about 20% by weight of one or more additives selected from the group consisting of alkaline agents, penetrating agents, chelating agents, wetting agents, conditioning agents, and fragrances, and
  e. water forming the balance;

B. placing the hair on rods or rollers;

C. applying the permanent waving lotion to the hair;

D. allowing the permanent waving lotion to remain on the hair for between about 5 and 30 minutes;

E. removing the permanent waving lotion from the hair by rinsing and towel blotting;

F. forming a dye additive composition comprising
  a. between about 0.01% and 5% by weight of one or more dyestuffs selected from imparting the desired coloring to the hair,
  b. between about 0.001% and 2.5% by weight of a lipotropic material,
  c. up to 15% by weight of one or more additives selected from the group consisting of ethanolamine, ethoxydiglycol, glycoproteins, hydroxyethylcellulose, PEG-8 hydrogenated tallow amine, tetrasodium EDTA, and fragrances, and
  d. water forming the balance;

G. forming a neutralizer composition comprising
  a. between about 1.0% and 3.0% by weight of hydrogen peroxide,
  b. between about 0.001% and 2% by weight of silk amino acids,
  c. between about 0.001% and 5% by weight of water soluble or emulsifiable silicone based compounds, and
  d. water forming the balance;

H. intermixing the dye additive composition with the neutralizer composition to form a dyeing and neutralizing composition;

I. adjusting the pH of the dyeing and neutralizing composition to range between about 7.0 and 9.0;

J. applying a portion of the dyeing and neutralizing mixture to the hair;

K. allowing the dyeing and neutralizing mixture to remain on the hair for between about 3 and 8 minutes;

L. removing the rods from the hair;

M. applying the remainder of the dyeing and neutralizing mixture to the rod-free hair;

N. allowing the dyeing and neutralizing mixture to remain on the hair for between about 5 and 15 minutes;

O. warming the hair to a temperature ranging between about 40° C. and 65° C. during at least a portion of the time that the dyeing and neutralizing mixture is on the rod-free hair;

P. allowing the hair to cool for between about 1 and 2 minutes; and

Q. rinsing the dyeing and neutralizing mixture from the hair; thereby attaining a permanently waved head of hair which also incorporates the precisely desired color imparted to the hair fibers in a manner which provides both uniformity and durability.

18. A system for simultaneously permanently waving and coloring hair, said system consisting essentially of:

A. a permanent wave lotion for application to the hair for breaking the disulfide linkages in the hair, said lotion consisting essentially of
  a. between about 6% and 25% by weight of a reducing agent selected from the group consisting of thioglycolate salts and esters of thioglycolate salts,
  b. between about 0.001% and 2.0% by weight of a silk amino acid,
  c. between about 0.001% and 5.0% by weight of one or more water soluble or emulsifiable silicone based compounds selected from the group consisting of dimethicones, amodimethicones, dimethicone copolyol, stearyoxytrimethylsilane, stearyoxydimethicones, quarternized silicone compounds, and betain silisone compounds,
d. up to 20% by weight of one or more additives selected from the group consisting of alkaline agents, penetrating agents, chelating agents, wetting agents, conditioning agents and fragrances, and
e. water forming the balance; and B. a dyeing and neutralizing composition for application to the hair after the removal of the permanent waving lotion, said dyeing and neutralizing composition being formed by intermixing
   a. a dye additive composition comprising
      1. between about 0.001% and 5% by weight of one or more dyestuffs for providing the desired color to the hair selected from the group consisting of HC Blue No. 2, HC Blue No, 4, HC Blue No. 5, HC Orange No. 1, HC Red No. 1, HC Red No. 3, HC Yellow No. 2, HC Yellow No. 3, HC Yellow No. 4, HC Yellow No. 5, Disperse Black 9, Disperse Blue 1, Disperse Blue 3, Disperse Violet 1, Disperse Violet 4, and Acid Orange No. 3,
      2. between about 0.001% and 2.5% by weight of a lipotropic material comprising vegetable-derived amino acids amidified with and containing one or more moieties selected from the group consisting of cocoyl-methylamine, lauryl, and stearoxyl,
      3. an alkali for maintaining the pH of the dyeing and neutralizing composition to between about 7 and 9, and
      4. water forming the balance; and
   b. a neutralizing composition comprising
      1. between about 1.0% and 3.0% by weight of hydrogen peroxide, and
      2. water forming the balance: whereby the serial application of the permanent waving lotion and the dyeing and neutralizing composition provides permanent waving of the hair and simultaneous dyeing thereof with a durable, long-lasting, semi-permanent coloring being imparted thereto.

19. The system defined in claim 18, wherein the additives of the permanent waving lotion are further defined as comprising:
    f. between about 1% and 2% by weight of ammonium chloride,
    g. between about 1% and 5% by weight of ammonia,
    h. between about 1% and 4% by weight of laureth-23 of the general formula $CH_3(CH_2)_{10}CH_2(OCH_2CH_2)_nOH$, wherein n has an average value of 23,
    i. between about 0.001% and 5% by weight of propylene glycol,
    j. between about 0.001% and 1% by weight of octoxynol-40 of the general formula $C_8H_{17}C_6H_4(OCH_2CH_2)_nOH$, wherein n has an average value of 40,
    k. between about 0.001% and 1% by weight of isolaureth-6 of the general formula $C_{12}H_{25}(OCH_2CH_2)_nOH$, wherein n has an average value of 6, and
    l. between about 0.5% and 2% by weight of a fragrance.

20. The system defined in claim 18, wherein the additives are further defined as comprising
    f. between about 2% and 5% by weight of ammonia,
    g. between about 0.001% and 3% by weight of styrene/acrylate copolymer,
    h. between about 1% and 4% by weight of laureth-23 of the general formula $CH_3(CH_2)_{10}CH_2(OCH_2CH_2)_nOH$, wherein n has an average value of 23,
    i. between about 0.001% and 1% by weight of octoxynol-40 of the general formula $C_8H_{17}C_6H_4(OCH_2CH_2)_nOH$, wherein n has an average value of 40,
    j. between about 0.001% and 1% by weight of isolaureth-6 of the general formula $C_{12}H_{25}(OCH_2CH_2)_nOH$, wherein n has an average value of 6, and
    k. between about 0.5% and 2% by weight of a fragrance.

21. The dyeing and neutralizing composition defined in claim 18, wherein said dye additive composition further comprises
    5. up to 1% by weight of ethanolamine,
    6. up to 2% by weight of ethoxydiglycol,
    7. up to 2% by weight of glycoproteins,
    8. up to 2% by weight of hydroxyethylcellulose,
    9. up to 5% by weight of PEG-8 hydrogenated tallow amine,
    10. up to 1% by weight of tetrasodium EDTA, and
    11. up to 2% by weight of a fragrance.

22. The neutralizer composition defined in claim 21, wherein said neutralizer is further defined as comprising
    3. between about 0.001% and 5% by weight of a water soluble or emulsifiable silicone based compound,
    4. between about 0.001% and 2% by weight of silk amino acid,
    5. up to 2% by weight of sodium lauryl sulfate,
    6. up to 2% by weight of cetearyl alcohol,
    7. up to 2% by weight of ceteth-20 of the general formula $CH_3(CH_2)_{14}CH_2(OCH_2CH_2)_nOH$, wherein n has an average value of 20,
    8. up to 2% by weight of mineral oil,
    9. up to 2% by weight of disodium phosphate,
    10. up to 2% by weight of phosphoric acid,
    11. up to 2% by weight of olealkonium chloride,
    12. up to 1% by weight of octoxynol-40 of the general formula $C_8H_{17}C_6H_4(OCH_2CH_2)_nOH$, wherein n has an average value of 40,
    13. up to 1% by weight of isolaureth-6 of the general formula $C_{12}H_{25}(OCH_2CH_2)_nOH$, wherein n has an average value of 6,
    14. up to 5% by weight of propylene glycol,
    15. up to 2% by weight of methyl parabin, and
    16. up to 2% by weight of a fragrance.

* * * * *